(12) United States Patent
Leonhardt (10) Patent No.: US 11,878,161 B2
(45) Date of Patent: Jan. 23, 2024

(54) COL17A1 MODULATION

(71) Applicant: Leonhardt Ventures LLC, Corona Del Mar, CA (US)

(72) Inventor: Howard J. Leonhardt, Corona Del Mar, CA (US)

(73) Assignee: Leonhardt Ventures LLC

(*) Notice: Subject to any disclaimer, the term of this patent is extended or adjusted under 35 U.S.C. 154(b) by 287 days.

(21) Appl. No.: 17/161,514

(22) Filed: Jan. 28, 2021

(65) Prior Publication Data

US 2021/0228870 A1 Jul. 29, 2021

Related U.S. Application Data

(60) Provisional application No. 62/967,337, filed on Jan. 29, 2020.

(51) Int. Cl.
| | | |
|---|---|---|
| *A61N 1/32* | (2006.01) | |
| *A61M 37/00* | (2006.01) | |
| *A61M 39/02* | (2006.01) | |
| *A61N 1/36* | (2006.01) | |

(52) U.S. Cl.
CPC ......... *A61N 1/328* (2013.01); *A61M 37/0015* (2013.01); *A61M 39/0208* (2013.01); *A61N 1/326* (2013.01); *A61N 1/327* (2013.01); *A61N 1/36014* (2013.01); *A61N 1/36034* (2017.08)

(58) Field of Classification Search
CPC ........ A61N 1/328; A61N 1/326; A61N 1/327; A61N 1/36014; A61N 1/36034; A61N 1/0496; A61M 37/0015; A61M 39/0208
See application file for complete search history.

(56) References Cited

U.S. PATENT DOCUMENTS

| | | | |
|---|---|---|---|
| 8,639,361 B2 | 1/2014 | Nathanson | |
| 8,945,104 B2 | 2/2015 | Boone et al. | |
| 9,533,170 B2 | 1/2017 | Dye et al. | |
| 9,855,418 B2 | 1/2018 | Haralambidis | |
| 10,646,644 B2 | 5/2020 | Leonhardt et al. | |
| 2003/0220556 A1 | 11/2003 | Porat et al. | |
| 2005/0113879 A1 | 5/2005 | Schuler et al. | |
| 2006/0030908 A1 | 2/2006 | Powell et al. | |
| 2008/0195181 A1* | 8/2008 | Cole ...................... | A61N 1/328 607/74 |
| 2013/0073001 A1* | 3/2013 | Campbell ............ | A61N 5/0616 607/88 |
| 2017/0028184 A1 | 2/2017 | Godden et al. | |

(Continued)

FOREIGN PATENT DOCUMENTS

| | | |
|---|---|---|
| EP | 0603451 A1 | 6/1994 |
| WO | 2006/116728 A2 | 11/2006 |
| WO | 2014/172693 A2 | 10/2014 |

OTHER PUBLICATIONS

Boyle, "Wound Treating-Jelly Regenerates Fresh, Scar-Free Skin," (Dec. 15, 2011), 2 pages.

(Continued)

*Primary Examiner* — Mallika D Fairchild
(74) *Attorney, Agent, or Firm* — TraskBritt (57) ABSTRACT

Described is a low voltage, pulsed electrical stimulation device for controlling expression of Collagen Type XVII Alpha 1 chain (COL17A1), a useful protein, by tissues. Also described are methods of COL17A1 in cells.

20 Claims, 6 Drawing Sheets

(56) References Cited

U.S. PATENT DOCUMENTS

2019/0015661 A1* 1/2019 Leonhardt ............ A61N 1/327
2020/0289541 A1 9/2020 Nishimura et al.

OTHER PUBLICATIONS

Bradshaw et al., "Designer Self-Assembling hydrogel Scaffolds Can Impact Skin Cell Proliferation and Migration," Sci. Rep., vol. 4, 6903, (2014), pp. 1-6.

Brooks et al., "Bioelectric Impedance Predicts Total Body Water, Blood Pressure, and Heart Rate During Hemodialysis in Children and Adolescents," Research Brief, vol. 18, Issue 3, (May 1, 2008), pp. 304-311.

Chernet et al., "Transmembrane Voltage Potential is an Essential Cellular Parameter for the Detection and Control of Tumor Development in a Xenopus Model," Disease Models & Mechanisms, vol. 6, (2013), pp. 595-607.

Columbia Implant Procedure Concepts, Medical Education, Pacemaker, ICD and CRT Overview, Boston Scientific Corporation, (2007), 23 pages.

Follicle Thought, COL17A1, Foxc1, Brotzu: Weekly Thoughts Feb. 8, 2016, 6 pages.

Gonzalez et al., "Platelet-Derived Growth Factor Signaling Modulates Adult Hair Follicle Dermal Stem Cell Maintenance and Self-Renewal," Nature Partner Journals, Regenerative Medicine (2017), pp. 1-12.

Hopkins Medicine "Overview of Pacemakers and Implantable Cardioverter Defibrillators (ICDs)," hopkinsmedicine.org/healthlibrary/conditions/cardiovascular_diseases/overview_of_pacemakers_and_implantable_cardioverter_defibrillators_icds_85,P00234/.

Hu et al. "Exosomes derived from human adipose mesenchymal stem cells accelerates cutaneous wound healing via optimizing the characteristics of fibroblasts", Nature Scientific Reports, vol. 6, Article No. 32993 (2016).

Hussein "Forever young: Study uncovers protein that keeps skin youthful" The Jakarta Post (Apr. 4, 2019).

Jouybar et al., "Enhanced Skin Regeneration by Herbal Extract-Coated Poly-L-Lactic Acid Nanofibrous Scaffold," Artif. Organs, vol. 41, No. 11, (2017), pp. E296-E307.

Liu et al., "Stem Cell Competition Orchestrates Skin Homeostasis and Ageing," Nature, vol. 568, (2019), pp. 344-350.

Mainichi, "Thinning Hair Caused by Decrease in Protein: Researches," (Feb. 5, 2016), 2 pages.

Mao et al., "13—Hydrogel fibrous scaffolds for accelerated wound healing," Electrofluidodynamic Technologies (EFDTs) for Biomaterials and Medical Devices, (2018), pp. 251-274.

Matsumura et al., "Hair Follicle Aging is Driven by Transepidermal Elimination of Stem Cells via COL17A1 Proteolysis," Science, vol. 351, No. 6273, aad4395 (2016).

Pierce et al., "Collection and Characterization of Amniotic Fluid from Scheduled C-Section Deliveries," Cell and Tissue Banking, (2016), 15 pages.

Prochazka et al. "Cocktail of Factors from Fat-derived Stem Cells Shows Promise for Critical Limb Ischemia" http://www.sciencenewsline.com/news/2016012204520017.html (Jan. 21, 2016).

Prochazka et al., "Therapeutic Potential of Adipose-Derived Therapeutic Factor Concentrate for Treating Critical Limb Ischemia," Cell Transplantation, vol. 25, (2016), pp. 1623-1633.

Salcedo et al., "Low Current Electrical Stimulation Upregulates Cytokine Expression in the Anal Sphincter," Int. J. Colorectal Dis., (2011), 6 pages.

Schmidt, "Scientists Uncover a Protein That Seems to Fight Aging in Our Skin," Science That Matters, (2019) 3 pages.

Shirai et al., "Expression of Anti-Aging Type-XVII Collagen (COL17A1/BP180) in Hair Follicle-Associated Pluripotent (HAP) Stem Cells During Differentiation," Tissue Cell., (2019), pp. 33-38.

Veiga et al., "Parasacral Transcutaneous Electrical Stimulation for Overactive Bladder in Children: An Assessment per Session," J. Pediatr Urol., vol. 12, No. 5, (2016), pp. 293.e1-293.e5.

Wang et al., "Local and sustained miRNA delivery from an injectable hydrogel promotes cardiomyocyte proliferation and functional regeneration after ischemic injury," Nat. Biomed. Eng., vol. 1, (2017), pp. 983-992.

Wu et al., "MSC-Exosome: A Novel Cell-Free Therapy for Cutaneous Regeneration," Rev. Article, vol. 20, Issue 3, (Mar. 1, 2018), pp. 291-301.

Zhang et al., "Exosomes derived from human embryonic mesenchymal stem cells promote osteochondral regeneration," Osteoarthritis and Cartilage, vol. 24, (2016), pp. 2135e2140.

* cited by examiner

*FluidSync™ M200 micropump*

COL17A1 MODULATION

CROSS-REFERENCE TO RELATED APPLICATION

This application claims the benefit under 35 U.S.C. § 119(e) of U.S. Provisional Patent Application Ser. No. 62/967,337, filed Jan. 29, 2020, the disclosure of which is hereby incorporated herein in its entirety by this reference.

TECHNICAL FIELD

The application relates generally to the field of medical devices and associated treatments, and more specifically to precise bioelectrical stimulation of a subject's tissue, possibly augmented with the administration of a composition comprising, among other things, stem cells and nutrients, useful to stimulate and treat the subject, the subject's tissue(s), the subject's organ(s), and/or the subject's cells. More specifically, the application relates to a device having programmed bioelectric signaling sequences, and associated methods for the controlled modulation of COL17A1 via precise bioelectrical signaling sequences useful in, for example, skin and hair applications as well as tissue regeneration applications.

BACKGROUND

Mutations in the human collagen XVII gene, COL17A1, lead to the absence or structural alterations and mutations of collagen XVII. COL17A1 was also known as BA16H23.2, BP180, BPA-2, BPAG2, LAD-1, ERED, collagen type XVII alpha 1, and collagen type XVII alpha 1 chain. Collagen Type XVII Alpha 1 chain ("COL17A1") is a transmembrane protein that plays an important role in maintaining the linkage between the intracellular and the extracellular structural elements involved in epidermal adhesion.

Mutations in the human collagen XVII gene, COL17A1, lead to the absence or structural alterations and mutations of collagen XVII, which result in diminished epidermal adhesion and skin blistering in response to minimal shearing forces. The disorder caused by biallelic COL17A1 mutations and is called "junctional epidermolysis bullosa". Collagen XVII also plays a role as an autoantigen in Bullous pemphigoid and herpes gestationis.

Matsumura et al. described that the thinning and loss of hair are prominent aging phenotypes with an unknown mechanism. They showed that hair follicle stem cell ("HF SC") aging causes the stepwise miniaturization of hair follicles and eventual hair loss. In vivo fate analysis of HFSCs revealed that the DNA damage response in HFSCs causes proteolysis of type XVII collagen (COL17A1/BP180), a critical molecule for HFSC maintenance, to trigger HFSC aging. Aged HFSCs are cyclically eliminated from the skin through terminal epidermal differentiation, thereby causing hair follicle miniaturization. The aging process can be recapitulated by COL17A1 deficiency and prevented by the forced maintenance of COL17A1 in HFSCs, demonstrating that COL17A1 in HFSCs orchestrates the stem cell-centric aging program of the epithelial mini-organ. Matsumura et al. "Hair follicle aging is driven by transepidermal elimination of stem cells via COL17A1 proteolysis" *Science*, Vol. 351, Issue 6273, aad4395 (2016).

Likewise, COL17A1 was also found to significantly promote wound repair of the skin. See, e.g., S. Hussein "Forever young: Study uncovers protein that keeps skin youthful" *The Jakarta Post* (Apr. 4, 2019).

BRIEF SUMMARY

Described herein is a bioelectric stimulator particularly configured to modulate (upregulate/downregulate) COL17A1 in cellular tissue via application of a bioelectric signal.

In order to upregulate COL17A1, the bioelectric signal preferably has a frequency of 25 Hz (+/−10-20 Hz) at 10 mV to 100 mV, for example, a 10 mV, 25 Hz, biphasic, square-wave pulse with a 50% duty cycle. In certain embodiments, COL17A1 was upregulated at 5,000 Hz.

In certain embodiments, a frequency range (+/−10-20 Hz) centered about frequency signal 25 Hz is used (e.g., 25 Hz+/−20 Hz at 10-100 mV).

In order to downregulate COL17A1, the bioelectric signal can be a frequency of 50 Hz (+/−10-20 Hz) at 60 mV to 100 mV, for example, a 100 mV, 50 Hz, biphasic, square-wave pulse with a 50% duty cycle. Alternatively, in order to downregulate expression and/or release of COL17A1, the bioelectric signal can be a frequency of 75 Hz (+/−10-20 Hz) at 100 mV, biphasic, square-wave pulse with a 50% duty cycle. In certain embodiments, COL17A1 was downregulated at 250,000 Hz.

Also described is a bioelectric stimulator including: a power source (e.g., battery, capacitor, or other suitable source of electricity), and means for delivering an electrical signal to a subject's tissue (e.g., via electrode(s) or wirelessly). The bioelectric stimulator utilizes the electrical signal to precisely control protein expression in the tissue on demand.

In certain embodiments, the bioelectric stimulator programmed to modulate COL17A1 is further configured to activate expression and/or release of insulin-like growth factor 1 ("IGF-1"), epidermal growth factor ("EGF"), hepatocyte growth factor ("HGF"), platelet-derived growth factor ("PDGF"), endothelial NOS ("eNOS"), vascular endothelial growth factor ("VEGF"), activin A, activin B, follistatin, interleukin 6 ("IL-6"), hypoxia-inducible factor 1-alpha ("HIF-1-α"), tropoelastin, and any combination thereof from the cellular tissue.

While not intending to be bound by theory, the described system utilizes precise bioelectric signaling sequences that appear to communicate with DNA and cell membranes within stimulated tissues of the subject to cause the cells to produce high volumes of collagen XVII. Useful indications (particularly for upregulation of COL17A1) include skin and muscle regeneration and treatment, collagen enhancement, hair loss reduction, treating psoriasis, and breast cancer. In certain embodiments, COL17A1 is utilized to aid in the rebuilding of a healthy compliant smooth muscle wall of the bladder. Potential indications for downregulation of COL17A1 include the management of junctional epidermolysis bullosa, Bullous pemphigoid, and herpes gestationis. For such indications, duration of treatment can be, for example, 20 to 40 minutes twice a week for 4 weeks, and then 20 to 40 minutes once a month until desired results are reached.

DETAILED DESCRIPTION

In certain embodiments, described is a bandage wrap that is applied to the affected region. A micro-stimulator may be located conveniently in the bandage wrap and is utilized to distribute specific bioelectric signals to the affected tissue and nerves that regulate various protein expressions for stem cell homing, stem cell proliferation, stem cell differentiation, blood vessel formation, blood circulation improvement, muscle function repair, and DNA repair.

Figure 1:
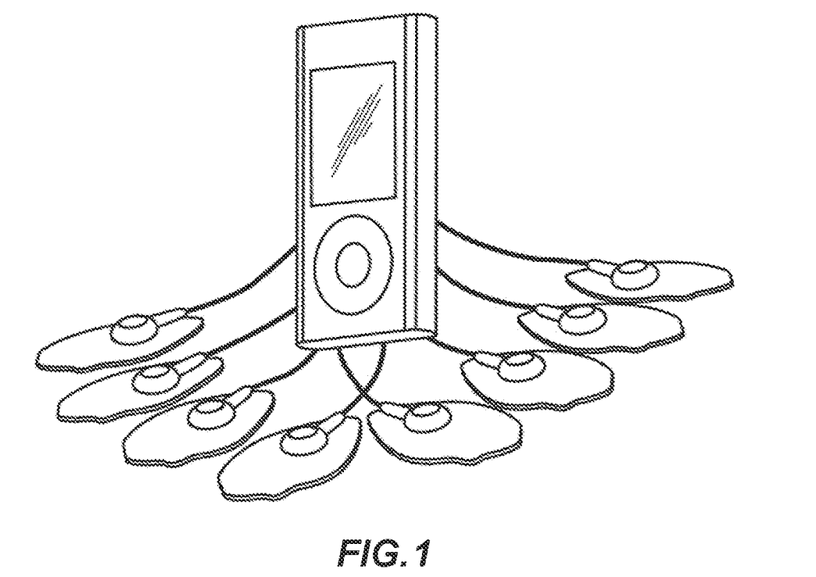
FIG. 1 depicts a programmed bioelectric stimulator for delivery to a subject connected to multiple soft conductive electrode pads.
Figure 2:
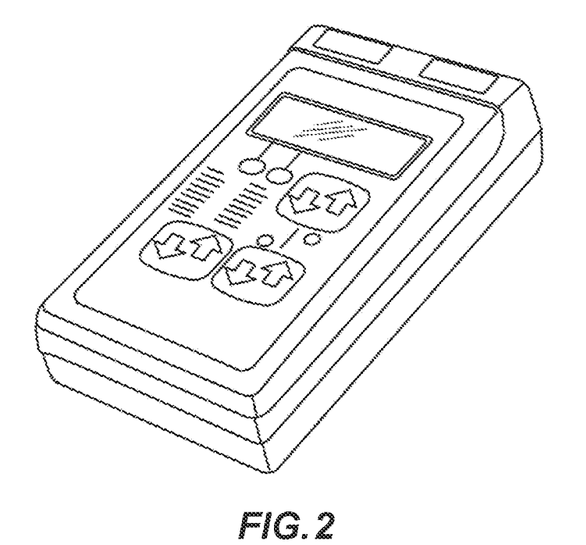
FIG. 2 depicts a programmed bioelectric stimulator as described herein.
Figure 3:
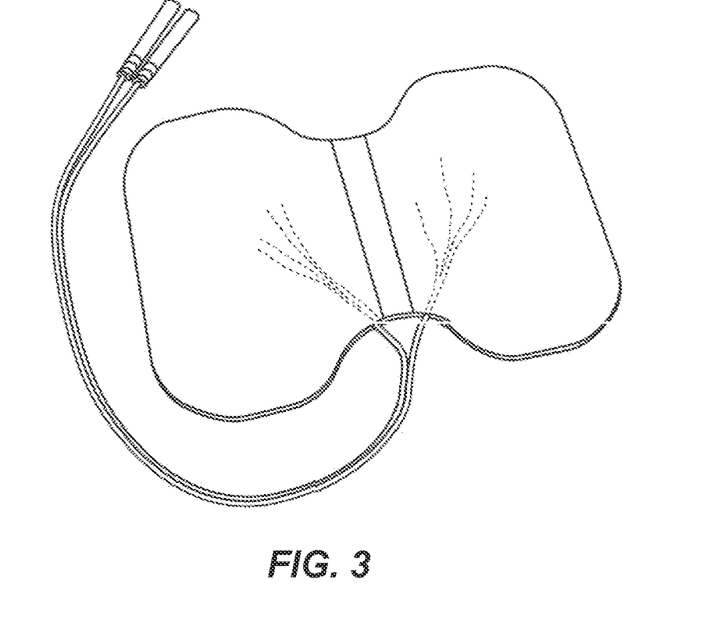
FIG. 3 depicts a conductive soft wrap for use with the system.
Figure 4:
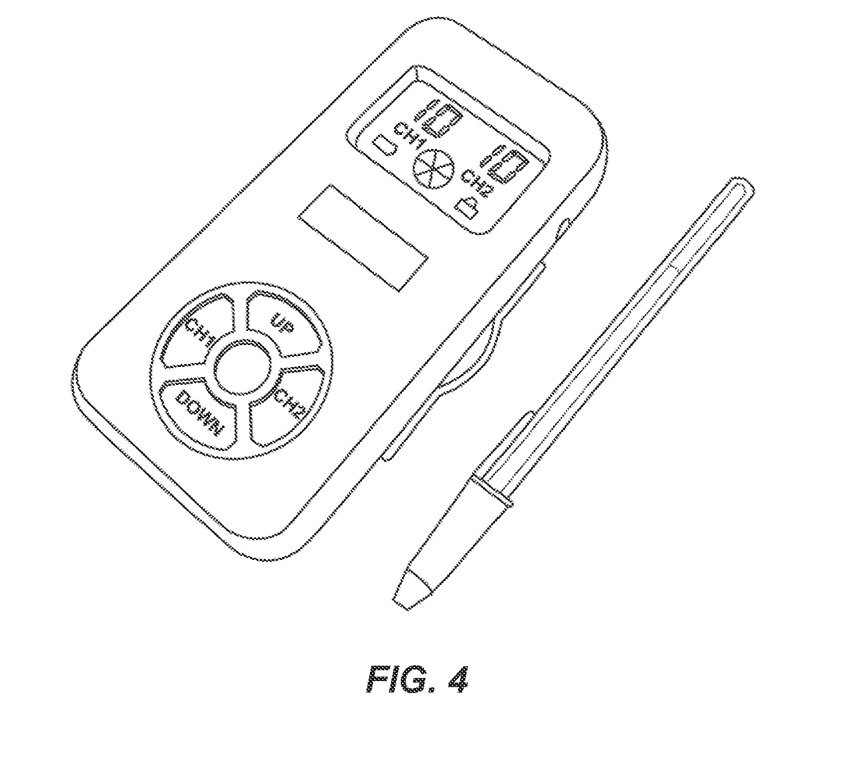
FIG. 4 depicts a programmed bioelectric stimulator depicted alongside a pen.
Figure 5:
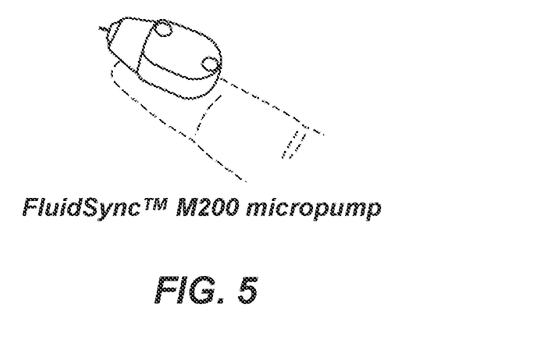
FIG. 5 depicts a micropump for potential use with the system.

Referring now to FIGS. 1-4, depicted is a stimulator for use in treating a human. The depicted device is about the size of a pen (FIG. 4) and is programmable. FIG. 5 depicts a micropump that may be used with the system to deliver a desired (and preferably complementary composition), such as a hereinafter described skin regeneration composition. The stimulator portion is preferably about the size of two quarters (available from QIG Greatbatch/Greatbatch, Inc. of Frisco, TX, US).

Figure 6:
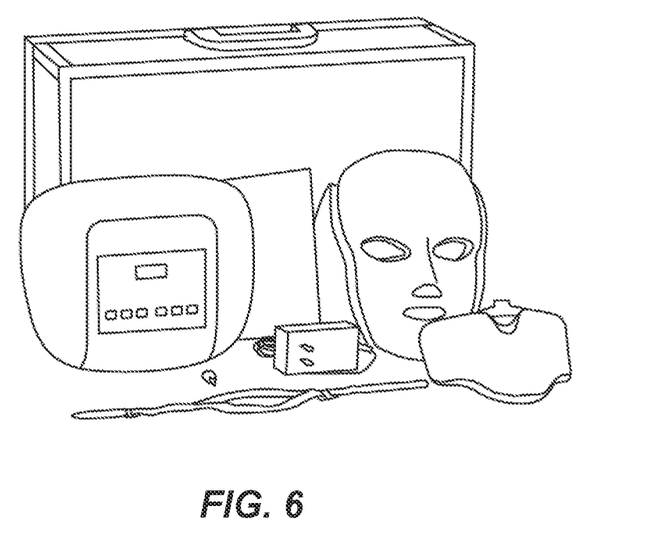
FIG. 6 depicts a programmed bioelectric stimulator together with a facemask and neck applicator. The facemask delivers bioelectric signals as well as LED light to the subject's face and neck.

Referring to FIG. 6, depicted is a human use stimulator and facemask for use with treatment of a subject's face and neck. Depicted particularly in FIG. 6 are the face and neck mask (with straps), controller/stimulator, and carrying case.

Micro stimulators may be purchased or constructed in the same manner heart pacemakers have been made since the 1960's. When used with a micro infusion pump (FIG. 5), such pumps can be purchased or produced similar to how they have been produced for drug, insulin, and pain medication delivery since the 1970's. The programming computer can be a standard laptop computer.

An exemplary microvoltage generator is available (for experimental purposes from Cal-X Stars Business Accelerator, Inc. DBA Leonhardt's Launchpads or Leonhardt Vineyards LLC DBA Leonhardt Ventures of Salt Lake City, UT, US). The primary difference is the special electrical stimulation signals needed to control, e.g., precise follistatin release on demand (which signals are described later herein). The leading pacemaker manufacturers are Medtronic, Boston Scientific Guidant, Abbott St. Jude, BioTronik and Sorin Biomedica.

Construction of the electric signal generators and pacemakers, are known in the art and can be obtained from OEM suppliers as well as their accompanying chargers and programmers. The electric signal generators are programmed to produce specific signals to lead to specific protein expressions at precisely the right time for, e.g., optimal organ treatment or regeneration.

The pacing infusion lead may be constructed or purchased from the same suppliers that build standard heart pacemaker leads. Pacing infusion leads may be purchased from a variety of OEM vendors. The pacing infusion lead may, for example, be a standard one currently used in heart failure pacing studies in combination with drug delivery.

An infusion and electrode wide area patch may be constructed by cutting conduction polymer to shape, and forming plastic into a flat bag with outlet ports in strategic locations.

Both wireless non-invasive and/or implantable wire lead ("electrode") based means may be used to deliver the regeneration and healing promoting bioelectric signals to target organs.

A wireless, single lumen infusion pacing lead or infusion conduction wide array patch may all be used to deliver the regeneration signals and substances to the organ/tissue of interest (e.g., the breast in the case of breast cancer) to be treated or they may be used in combination.

A re-charging wand for use herein is preferably similar to the pacemaker re-charging wand developed by Alfred Mann in the early 1970's for recharging externally implantable pacemakers.

Bioelectric stimulation can be done with the described microstimulator, which can have a pacing infusion lead with, e.g., a corkscrew lead placed/attached at, e.g., the center of the tissue to be stimulated and/or treated.

The microstimulator is actuated and runs through programmed signals to modulate the production of, e.g., collagen XVII. In such a method (and for upregulation), the electrical signal includes a frequency of 25 Hz (+/−10-20 Hz) at 10 mV to 100 mV, for example, a 10 mV, 25 Hz, biphasic, square-wave pulse with a 50% duty cycle. In order to downregulate COL17A 1, the bioelectric signal can be a frequency of 50 Hz (+/−10-20 Hz) at 60 mV to 100 mV, for example, a 100 mV, 50 Hz, biphasic, square-wave pulse with a 50% duty cycle. Alternatively, in order to downregulate expression and/or release of COL17A1, the bioelectric signal can be a frequency of 75 Hz (+/−10-20 Hz) at 100 mV, biphasic, square-wave pulse with a 50% duty cycle.

COL17A1 was upregulated 340% (standard deviation 20%; standard error 11%) with a bioelectric signal of 25 Hz, 10 mV in mouse chondrocytes.

In certain embodiments, the device provides bioelectric signaling sequences applied to the subject's skin are ones for (a) SDF-1 and/or PDGF (e.g., for stem cell homing to the treated area), (b) VEGF, PDGF, HIF-1-α, CXCL5, HGF, EGF, SDF1, and/or eNOS (e.g., for growing new blood vessels in the treated area), (c) tropoelastin (e.g., to increase the elasticity of skin in the treated area), (d) follistatin (e.g., to improve muscle tone in the treated area), and (e) IGF-1 (e.g., for DNA repair due to aging and sun damage in the treated area).

Preferably, a device provides bioelectric signaling sequences applied to the subject's skin are ones for (a) SDF-1 (stem cell homing), (b) tropoelastin (to turn back on the elasticity switch ("increase skin elasticity") that turns off at age 9 in humans), (c) IGF-1 (for DNA repair), (d) VEGF, SDF-1, HGF, EGF, PDGF, eNOS, HIF-1-α, CXCL5, tropoelastin, and/or EGF (for dermal skin repair), (e) IL's (for inflammation response/inflammation management), (f) BMP proteins, and (g) Activin A and/or B. See, e.g., Gonzalez et al. "Platelet-derived growth factor signaling modulates adult hair follicle dermal stem cell maintenance and self-renewal" *NPJ Regen Med.* 2017 Apr. 14; 2:11. doi: 10.1038/s41536-017-0013-4. PMID: 29302347; PMCID: PMC5665619.

In certain embodiments (e.g., for hair regrowth), Sonic Hedgehog is also utilized. N. Lavars "Scientists fire up sonic hedgehog gene to spawn new hair regrowth possibilities" *New Atlas* 57435 (Nov. 28, 2018).

In certain embodiments, a device provides bioelectric signaling sequences applied to the subject's skin are signals for (besides collagen XII): (a) SDF-1 (e.g., for stem cell homing to the treated area), (b) IGF-1 (e.g., for DNA repair due to aging and sun damage in the treated area), (c) tropoelastin (e.g., to increase the elasticity of skin in the treated area), and (d) VEGF (e.g., to improve blood circulation in the treated area). Preferably, such a device also provides bioelectric signaling sequences for application to the subject's skin for (e) PDGF, HIF-1-α, eNOS, and/or CXCL5, (e.g., to improve blood circulation in the treated area), (f) stem cell proliferation, (g) stem cell differentiation control, (h) extended PRF protein release, (i) HGF (e.g., to enhance skin regeneration), and/or (j) EGF (e.g., to aid or enhance skin regeneration).

The device may be similar in construction and form to the NuFace® device of WO2006/116728 (Nov. 2, 2006), the contents of which are incorporated herein by this reference. The NuFace® device comprises a hand-held housing from which a pair of electrodes project and circuitry for establishing a potential difference between the electrodes so that a microcurrent flows between the electrodes when the electrodes are placed on the skin. For other devices adaptable for use with the herein described system see, e.g., EP 0603451 A1 to Paolizzi (Jun. 29, 1994) and U.S. Pat. No. 8,639,361 to Nathanson (Jan. 28, 2014), the contents of each of which are incorporated herein by this reference. Similar devices are the LightStim MultiWave™ device for LED light therapy.

While such devices may be adapted for use herein, these prior art microcurrent devices were generally designed to accelerate healing via "current of injury" signaling, to improve mildly blood circulation and muscle tone and provide mild pain relief. For example, traditional TENS devices were designed to lower pain. Nearly all of these devices have relatively fuzzy/noisy signals compared to new modern precise bioelectric signaling stimulators, such as those used and programmed herein. Traditional microcurrent facial devices do not have specific, precise signals or sequences for controlling the release of specific regeneration promoting proteins on demand. Furthermore, even if they were programmed with these signals, they do not have the clarity of signal for the body to understand the instruction. Bioelectrical stimulators, such as those described herein, have precise programming to deliver precise clear signals to control protein expressions on demand. These controlled protein expressions are for very specific purposes.

In certain embodiments, the bioelectrical stimulation is provided by a SkinStim Model 240 High Precision Bioelectric and TENS Stimulator, which is pre-programmed for controlled expression of collagen XVII, SDF-1, VEGF, IGF-1, and tropoelastin. Bioelectric microcurrent and LED Face Mask (inner and outer views) such as a SkinStim Model 100 Micro-current and LED face mask may be used to treat the forehead, eyebrow, cheek, under-eye, jaw line, and jowls. Such a device (FIG. 6) preferably has, e.g., neoprene masks and straps (which are soft and oil and water resistant), a silicone outer casing of micro-current nodes and strap clasps, LED lights—rings that light up when mask is turned on, and metal nodes and wiring on inside of mask for micro-current.

In certain embodiments, a microcurrent and LED Mini-Mask Model 200 micro-current mini face mask is used. For applications just about the subject's eyes, a SkinStim Eye-Mask Model 100 microcurrent Eye mask may be used.

In certain embodiments, a pulsed laser light generator (e.g., one available from Epimedica of San Clemente, CA, US) is used to provide laser light therapy to the area to be treated.

Methods and benefits of utilizing light and light emitting diodes (LEDs) for phototherapeutic treatment are described in U.S. Pat. No. 9,533,170 (Jan. 3, 2017) to Dye et al., U.S. Pat. No. 8,945,104 (Feb. 3, 2015) to Boone, III et al., and US 2006/0030908 A1 (Feb. 9, 2006) to Powell et al., the contents of each of which are incorporated herein by this reference.

Delivery may also/alternatively be through a micro-current facial conductive massage glove wherein, for example, electrodes associated with the bioelectrical stimulator are used to apply the desired electrical therapies.

Further, bioelectric signals may be used to improve muscle tone (follistatin for muscle tone improvement) and with improved muscle tone, the appearance of the overlying skin improves. Likewise, bioelectric signals may also be used to improve blood flow (VEGF, eNOS, PDGF, and HIF-1-α for blood circulation improvement). IGF-1, EGF, HGF, Activin A+B, Follistatin and PDGF are expressed via bioelectric signaling and are intended to promote skin regeneration and DNA repair.

Typical subjects to be treated are humans, typical tissues are skin, hair and tissue regeneration, and typical areas of, for example, the skin are the face, neck, arms, the back of hands, legs, breast(s), etc.

"Skin regeneration compositions" include basic skin regeneration compositions and advanced skin regeneration compositions. A basic skin regeneration composition contains, e.g., amniotic fluid and membranes, platelet rich fibrin ("PRF") and PRF membranes, and nutrient engineered hydrogel. An advanced skin regeneration composition typically contains autologous (from patient to patient) and/or homologous stem cells (adipose-derived), ECM—matrix (skin matrix), micro RNAs, selected exosomes, selected alkaloids (e.g., tetraharmine), and oxygenated nanoparticles.

For instance, in certain embodiments, the skin regeneration composition contains bioelectric pre-treated stem cells (e.g., adipose tissue-derived), stromal fraction ("SVF"), platelet rich fibrin ("PRF"), selected growth factors, amniotic fluid, exosomes, micro RNAs in a gel, nutrient hydrogel, oxygenated nanoparticles, and skin matrix.

Stem cells may be obtained using a same-day stem cell process, which takes about 60 minutes. In such a process, first, one obtains tissue sample from the subject. Then a fat sample is processed using commercially available equipment and kits. This tissue is combined with reagent centrifuge and platelet rich fibrin. The stromal vascular fraction ("SVF") is washed and filtered. Stem cells are re-suspended in saline or platelet rich plasma ("PRP") and injected into the subject. The process may be repeated as needed or desired.

The SVF of adipose tissue is a source of pre-adipocytes, mesenchymal stem cells (MSC), endothelial progenitor cell, T cells, B cells, mast cells as well as adipose tissue macrophages.

Elements found in a skin regeneration composition may also delivered via cellular stimulation with bioelectric signals. Thus, the described system may be combined with bioelectric PRF and bioelectric amnio-fluid and bioelectric stromal fraction.

PRF may be provided by utilization of a SkinStim Bedside PRF Device or other platelet rich fibrin processing device.

This composition is preferably delivered repeatedly with a DermaPen™-like microneedle array over time. One such microneedle system is disclosed in US20170028184A1 to Godden et al. (Feb. 2, 2017) for a "Device and method of skin care and treatment via microneedles having inherent anode and cathode properties, with or without cosmetic or pharmacological compositions", the contents of which are incorporated herein by this reference in its entirety.

A skin matrix is a composition comprising skin cells that are to be treated. The skin matrix is believed to aid in stem cell differentiation, but in any event is found to be useful in the composition. It has been found that for the multicomponent composition, cells plus selected growth factors are better than just cells alone. See, e.g., Prochazka et al. "Therapeutic Potential of Adipose-Derived Therapeutic Factor Concentrate for Treating Critical Limb Ischemia," Cell Transplantation, 25(9), pp. 1623-1633(11) (2016) and "Cocktail of Factors from Fat-derived Stem Cells Shows Promise for Critical Limb Ischemia," world wide web at sciencenewsline.com/news/2016012204520017.html (Jan. 22, 2016), the contents of each of which are incorporated herein by this reference.

Useful hydrogels (and microRNA) are known and are described in Mao et al. "13—Hydrogel fibrous scaffolds for accelerated wound healing" *Electrofluidodynamic Technologies (EFDTs) for Biomaterials and Medical Devices*, pages 251-274 (2018), Bradshaw et al. "Designer self-assembling hydrogel scaffolds can impact skin cell proliferation and migration" *Nature Scientific Reports*, vol. 4, Article number: 6903 (2014), Wang et al. "Local and sustained miRNA delivery from an injectable hydrogel promotes cardiomyocyte proliferation and functional regeneration after ischemic injury", *Nat Biomed Eng.* 2017; 1: 983-992, doi: 10.1038/s41551-017-0157-y, R. Boyle "Wound-Treating Jelly Regenerates Fresh, Scar-Free Skin", *Popular Science*, (Dec. 15, 2011), "New material developed for accelerated skin regeneration in major wounds", *Science Highlight*, (National Institute of Biomedical Imaging and Bioengineering, Dec. 17, 2015), and Jouybar et al. "Enhanced Skin Regeneration by Herbal Extract-Coated Poly-L-Lactic Acid Nanofibrous Scaffold" *Artif Organs.* 2017 November; 41(11): E296-E307. doi: 10.1111/aor.12926.

Exosomes represent a specific subset of secreted membrane vesicles, which are relatively homogeneous in size (30-100 nm). Exosomes have been proposed to differ from other membrane vesicles by its size, density, and specific composition of lipids, proteins, and nucleic acids, which reflect its endocytic origin Exosomes are formed in endosomal vesicles called multivesicular endosomes (MVEs) or multivesicular bodies, which originate by direct budding of the plasma membrane into early endosomes. The generation of exosomes to form MVEs involves the lateral segregation of cargo at the delimiting membrane of an endosome and inward budding and pinching of vesicles into the endosomal lumen. Because exosomes originate by two successive invaginations from the plasma membrane, its membrane orientation is similar to the plasma membrane. Exosomes from many cell types may contain similar surface proteins as the cell from which it is derived. Membrane proteins that are known to cluster into microdomains at the plasma membrane or at endosomes, such as tetraspanins (CD63, CD81, CD82), often are also enriched in EVs. It is also thought that endosomal sorting complex responsible for transport system and tetraspanins, which are highly enriched in MVEs, play a role in exosome production. How cytosolic constituents are recruited into exosomes is unclear but may involve the association of exosomal membrane proteins with chaperones, such as HSC70, that are found in exosomes from most cell types. MVEs are also sites of miRNA-loaded RNA-induced silencing complex accumulation, and the fact that exosome-like vesicles are considerably enriched in GW182 and AGO2 implicates the functional roles of these proteins in RNA sorting to exosomes. Exosomes are released to the extracellular fluid by fusion of MVE to the plasma membrane of a cell, resulting in bursts of exosome secretion. Several Rab GTPases such as Rab 27a and Rab27b, Rab11 and Rab35, all seem to be involved in exosomes release.

Useful exosomes are known and described in Hu et al. "Exosomes derived from human adipose mesenchymal stem cells accelerates cutaneous wound healing via optimizing the characteristics of fibroblasts", *Nature Scientific Reports*, vol. 6, Article number: 32993 (2016), Zhang et al. "Exosomes derived from human embryonic mesenchymal stem cells promote osteochondral regeneration", *Osteoarthritis and Cartilage*, vol. 24, Issue 12, December 2016, pp. 2135-2140, and Wu et al. "MSC-exosome: A novel cell-free therapy for cutaneous regeneration", *Cytotherapy*, vol. 20, Issue 3, March 2018, pp. 291-301.

Generally, the system hereof involves a bioelectric stimulator controlling release of Collagen XVII, SDF-1, IGF-1, HGF, EGF, VEGF, PDGF, eNOS, follistatin, Activin A and B, and tropoelastin.

Collagen XVII is as described above. Follistatin promotes muscle growth and counteracts myostatin. IGF-1 is for DNA repair. PDGF is a second stem cell homing factor and helps tissue regeneration. SDF-1 is a powerful regeneration protein, as is IGF-1. SDF-1 is generally for recruiting stem cells and maturing blood vessels. HGF is for tissue regeneration. EGF grows tissue. VEGF grows blood vessels. PDGF is a second stem cell homing factor and helps tissue regeneration. eNOS dilates blood vessels. Follistatin promotes muscle growth. Activin A and B regenerates nerve cells and neurons. Tropoelastin increases elasticity of all tissues especially the skin. Any one of the protein expression signals work well on their own for organ regeneration, but they work better together.

The micro voltage signal generator may be produced utilizing the same techniques to produce a standard heart pacemaker well known to a person of ordinary skill in the art. An exemplary microvoltage generator is available (for experimental purposes from Cal-X Stars Business Accelerator, Inc. DBA Leonhardt's Launchpads or Leonhardt Vineyards LLC DBA Leonhardt Ventures of Salt Lake City, UT, US). The primary difference is the special electrical stimulation signals needed to control, e.g., precise follistatin release on demand (which signals are described later herein). The leading pacemaker manufacturers are Medtronic, Boston Scientific Guidant, Abbott St. Jude, BioTronik and Sorin Biomedica.

Construction of the electric signal generators and pacemakers, are known in the art and can be obtained from OEM suppliers as well as their accompanying chargers and programmers. The electric signal generators are programmed to produce specific signals to lead to specific protein expressions at precisely the right time for, e.g., optimal treatment or regeneration.

An infusion and electrode wide area pitch may be constructed by cutting conduction polymer to shape and forming plastic into a flat bag with outlet ports in strategic locations.

Any one of the protein expression signals work well on their own, but they work better together. SDF-1 is the most powerful regeneration protein followed by IGF-1.

A preferred composition includes adipose-derived cells (or bone marrow-derived MSCs or any pluripotent stem cell, such as iPS cells) and growth factor mix which should include, for example, SDF-1, IGF-1, EGF, HGF, PDGF, VEGF, eNOS, activin A, activin B, follistatin, and tropoelastin plus selected exosomes (miR-146a, miR-294, mES-Exo) plus selected alkaloids (harmine and tetrahydroharmine) plus selected anti-inflammatory factors plus nutrient hydrogel (IGF-1, SDF-1, HGF plus FGF) plus skin matrix. Also, preferably included are amniotic fluid, placenta, or cord blood when available.

The concentration of cells in the compositions is preferably about 50,000,000 cells/ml. The amniotic fluid is preferably as described in Pierce et al. "Collection and characterization of amniotic fluid from scheduled C-section deliveries," *Cell Tissue Bank*, DOI 10.1007/s10561-016-9572-7 (Springer, 2012) and is available from Irvine Scientific.

Described is a method of activating a tissue to differentiate a stem cell or to stimulate the tissue to produce a protein. The protein is selected from the group consisting of collagen XVII, insulin-like growth factor 1 ("IGF-1"), epidermal growth factor ("EGF"), hepatocyte growth factor ("HGF"), platelet-derived growth factor ("PDGF"), endothelial NOS ("eNOS"), vascular endothelial growth factor ("VEGF"), activin A, activin B, follistatin, interleukin 6 ("IL-6"), hypoxia-inducible factor 1-alpha ("HIF-1-$\alpha$"), and tropoelastin, the method including: stimulating the, e.g., human tissue with an electrical signal appropriate for the protein and tissue.

In such a method, when the electrical signal includes (within 15%): 0.1V applied at a frequency of about 50 Hz with a duration of about three (3) minutes (wherein the electrical signal is as measured three (3) mm deep into the tissue), the protein produced is VEGF.

In such a method, when the electrical signal includes (within 2%): 200 picoamps for about 10 seconds for about one (1) hour and the pulse has an amplitude of about 5 volts and a width of about 0.5 milliseconds for about 1 hour, with a duration of about one (1) minute (wherein the electrical signal is as measured three (3) mm deep into the tissue), stem cells differentiate.

In such a method, when the electrical signal includes (within 15%): 10V at 50 Hz and 100 Hz for about 12 hours each (duration 1 minute) (wherein the electrical signal is as measured three (3) mm deep into the tissue), the protein produced is follistatin.

In such a method, when the electrical signal includes (within 15%): 3.5 V stimulation in 10 second bursts, 1 burst every 30 seconds at a frequency of about 50 Hz (duration 5 minutes) (wherein the electrical signal is as measured three (3) mm deep into the tissue), the protein produced is HGF.

In such a method, when the electrical signal includes (within 15%): 3 mv with a frequency of about 22 Hz, and a current of about 1 mA for about fifteen (15) minutes and 3 ma for about fifteen (15) minutes (duration 5 minutes) (wherein the electrical signal is as measured three (3) mm deep into the tissue), the protein produced is IGF-1.

In such a method, when the electrical signal includes (within 15%): 0.06 V with 50 Hz alternating electrical field and a current of about 1 mA for about fifteen (15) minutes and 3 mA for about fifteen (15) minutes (duration 2 minutes) (wherein the electrical signal is as measured three (3) mm deep into the tissue), the protein produced is tropoelastin.

In such a method, when the electrical signal includes (within 15%): alternating high-frequency (HF) and medium-frequency signals (MF), symmetric, biphasic, trapezoid pulses, with 400-µs pulse duration and 1.5/1-s ramp-up/ramp-down duration, respectively (wherein the electrical signal is as measured three (3) mm deep into the tissue), the protein produced is eNOS. In such a method, when the HF consists of about 75 Hz pulses with six (6) seconds on and 21 seconds off for about fifteen (15) minutes. In such a method, when the MF consists of about 45 Hz pulses with 5 seconds on 12 seconds off for about fifteen (15) minutes followed by stimulation duration set as 20 minutes. In such a method, when the electrical signal includes (within 15%): 1 Hz stimulation, stimulation applied for about nine (9) seconds, followed by a one (1) second silent period, a total of about 1080 stimulations for about 20 minutes. In such a method, when the electrical signal includes (within 15%): 20 Hz stimulation, stimulation applied for about two (2) seconds, followed by silent period for about 28 seconds, a total of about 1600 stimulations for about 20 minutes (duration 2 minutes).

In such a method, when the electrical signal includes (within 15%): 6 mv at 150 Hz Monophasic square wave pulse 0.1 ms in duration current of fifteen (15) mA for about fifteen (15) minutes (duration two (2) minutes) (wherein the electrical signal is as measured three (3) mm deep into the tissue), the protein produced is Activin B.

In such a method, when the electrical signal includes (within 15%): 10 V/cm, pulse-width 180 µs, 500 Hz (duration nine (9) minutes) (wherein the electrical signal is as measured three (3) mm deep into the tissue), the protein produced is EGF.

For example, upregulation of IGF-1, VEGF, and SDF-1 was achieved in cardiomyocytes using such signals. Upregulation of SDF-1 was achieved in pig heart. Upregulation of VEGF, endothelial NOS ("eNOS"), hypoxia-inducible factor 1-alpha ("HIF-1-$\alpha$"), and IL-6 was achieved in eye cells.

Also described is a method of activating a tissue to produce stromal cell-derived factor 1 ("SDF-1"), the method including: stimulating the (e.g., human) tissue with an electrical signal, wherein the electrical signal includes (within 15%): 30 pulses per second with a voltage of about 3.5 mV, and successively alternating currents of about 700 to 1500 picoamps for about one minute, and again with 700 to 1500 picoamps for about one minute and stimulated with current of about 0.25 mA, pulse duration of about 40 pulses/s, pulse width of about 100 µs, wherein the electrical signal is as measured three (3) mm deep into the tissue (e.g., preferably for a period of time of about 20 minutes).

Further described is a method of activating a tissue to attract a stem cell, the method including: stimulating the (e.g., human) tissue with an electrical signal, wherein the electrical signal includes (within 2%): fifteen (15) mV and a current of about 500 picoamps at 70 pulses per minute for about three (3) hours and 20 pulses per minute, a pulse amplitude of from about 2.5-6 volts, and a pulse width of from about 0.2-0.7 milliseconds for about three (3) hours for about three (3) minutes, wherein the electrical signal is as measured three (3) mm deep into the tissue.

In some cases, SDF-1 recruits via a presumed homing signal new reparative stem cells to the damaged skin. VEGF causes new nutrient and oxygen producing blood vessels to grow into the area being treated. IGF-1 repairs damaged cells and tissues. Follistatin repairs damaged muscle. Tropoelastin adds elasticity to treated tissues making them more compliant. HGF aides in all repair processes. All of these proteins work together to fully regenerate/rejuventate the skin tissue over time.

The healing process can be accelerated with the use of a micro infusion pump that is filled with various types of stem cells and growth factors and in some cases drugs.

What follows are preferred signals from the stimulator. For example, described are two PDGF expression control signals, one low voltage and one higher voltage. The test tissue is sheep heart tissue. The test cells are mesenchymal stem cells.

30% PDGF increase: 3 V/cm, 10 Hz, 2 micro amps (0.000002 amps) and the pulse duration 0.2 ms.

230% PDGF increase: 20 V/cm 100 Hz, 0.25 mA (2.5e-7 amps) and pulse duration of 40 pulses/s, width of 100 µs.

40 minute treatment cycles 2 times a week for 4 weeks and then 3 times a week for 12 weeks.

PDGF Signal: 20V for 1 minute, 20 MVs for 10 minutes, current of 0.25 mA, pulse duration of 40 pulses/s, pulse width of 100 µs, and frequency of 100 Hz for 5 minutes followed by 528 Hz for 3 minutes and 432 Hz for 3 minutes and 50 Hz for 3 minutes.

VEGF—Blood vessel sprouting growth: 0.1V applied at a frequency of 50 Hz. Duration 3 minutes. In certain embodiments, the duration can be for a time of, e.g., from 10 to 40 minutes, wherein the percentage VEGF expression increases with time.

SDF-1—Stem cell recruiting signal: 30 pulses per second with a voltage of 3.5 mV, and successively alternating currents of 700 to 1500 picoamps for one minute, and again with 700 to 1500 picoamps for one minute and stimulated with current of 0.25 mA, pulse duration of 40 pulses/s, pulse width of 100 µs, and frequency of 100 Hz—each signal for 40 minutes to 8 hours a day for 2 to 36 months as needed for ideal results. Duration 7 minutes.

Stem cell proliferation signals: 15 mV and a current of 500 picoamps at 70 pulses per minute for 3 hours and 20 pulses per minute, a pulse amplitude of from 2.5-6 volts, and a pulse width of from 0.2-0.7 milliseconds for 3 hours. Duration 3 minutes.

Stem cell differentiation signals to become muscle: 200 picoamps for 10 seconds for 1 hour and the pulse has an amplitude of 5 volts and a width of 0.5 milliseconds for 1 hour. Duration 1 minute. Another method is to reverse polarity and drop the voltage.

Stem cell differentiation signal to become skin: low-voltage square wave with 60 ms pulse duration for one to seven cycles, then reverse polarity to a negative square wave for one to fourteen cycles, which repeats, delivering 200 micro-amps.

Follistatin—(muscle growth) production signal: 10V at 50 HZ and 100 HZ 0.25 mA. Duration 1 minute.

HGF—Hepatocyte growth factor (arrhythmia reduction) signal: 3.5V stimulation in 10 second bursts, 1 burst every 30 seconds at frequency 50 HZ. Duration 5 minutes.

IGF-1: 3 mv with electric frequency of 22 Hz, and electric current of 1 mA for 15 minutes and 3 ma for 15 minutes. Duration 5 minutes.

Tropoelastin: 0.06 V with 50Z alternating electrical field and electric current of 1 ma for 15 minutes and 3 ma for 15 minutes. Duration 2 minutes.

eNOS: Alternating high-frequency (HF) and medium-frequency signals (MF): Symmetric, biphasic, trapezoid pulses, with 400-µs pulse duration and 1.5/1-s ramp-up/ramp-down duration, respectively. HF consisted of 75 Hz pulses with 6 second on-21 second off for 15 minutes. MF consisted of 45 Hz pulses with 5 second on-12 second off for 15 minutes. Followed by stimulation duration set as 20 minutes for both 1 Hz and 20 Hz stimulations. For 1 Hz stimulation, stimulation is applied for 9 seconds, followed by a 1 second silent period, a total of 1080 stimulations for 20 min. For 20 Hz stimulation, stimulation is applied for 2 seconds, followed by silent period for 28 seconds, a total of 1600 stimulations for 20 min. Duration 2 minutes.

Activin B: 6 mv at 150 HZ Monophasic square wave pulse 0.1 ms in duration current of 15 mA for 15 minutes. Duration 2 minutes.

EGF—10 V/cm, pulse-width 180 µs, 500 Hz. Duration 9 minutes.

In certain embodiments, a subject's skin is first scanned or analyzed with a device to determine what his or her needs may be before treatment begins. The scanning/analysis can be by, e.g., generating mechanical vibrations at position adjacent the location to be an analyzed as described in, e.g., US 2003/0220556 A1 to Porat et al. (the contents of which are incorporated herein by this reference) and/or by measuring transmembrane voltage potential of a cell (see, e.g., Chernet & Levin, "Transmembrane voltage potential is an essential cellular parameter for the detection and control of tumor development in a *Xenopus* model," *Dis. Models & Mech.* 6, pp. 595-607 (2013); doi:10.1242/dmm.010835, the contents of which are also incorporated herein by this reference.) See, also, Brooks et al. "Bioelectric impedance predicts total body water, blood pressure, and heart rate during hemodialysis in children and adolescents" *J. Ren Nutr.*, 18(3):304-311 (May 2008); doi: 10.1053/j.jrn.2007.11.008, the contents of which are incorporated herein by this reference, describing the use of bioelectric impedance to evaluate the variability of blood pressure, systolic blood pressure, etc.

As used herein, "scanning" means measuring bioelectrical electrical activity of skin, sometimes by placement of a bion coil reader and transmitter in the skin, and direct that information to a computer. The computer stores the bioelectrical read measurements of diseased skin and healthy skin and makes a comparative exam classifying the skin into one category or another, which is much like a doctor using information to make a diagnosis.

Scanners such as the Ina'Chi scanner, the Quantum Magnetic Resonance Analyzer (QMRA), the 3D Quantum Health Analyzer Scan whole body organ health 2, Body Scan® scanner, and the "BIONic muscle spindle" are also useful.

In an alternative embodiment, the analysis conducted by the device comprises (or further includes) detecting minute energy fields around the human body with, e.g., a "SQUID magnetometer" (SQUID is an acronym for "Superconducting Quantum Interference Device"), able to detect biomagnetic fields associated with physiological activities in the subject's body. A quantum resonant magnetic analyzer analyzes such fields. The magnetic frequency and energy of a subject's tissue(s) are collected by appropriately positioning the sensor with respect to the portion of the subject's tissue(s) to be analyzed, and after amplification of the signal by the instrument, the data are compared with standard quantum resonant spectrum of diseases, nutrition, and other indicators/markers to determine whether the sample waveforms are irregular using a Fourier approach.

In certain embodiments, in addition to up or downregulation of COL17A1, bioelectric signaling is applied to the area of skin to be treated in approximate 28 minute treatment sessions twice a week for, e.g., up to 16 weeks (32 times total) utilizing, e.g., a benchtop bioelectric stimulator and face mask. The bioelectric signaling is preferably applied to the skin area to be treated as follows: (a) SDF-1 homing signal to recruit stem cells to skin for about seven (7) minutes, (b) IGF-1 DNA repair signal for about four (4) minutes, (c) tropoelastin signal to increase skin elasticity for about twelve (12) minutes, and (d) blood circulation improvement signal sequence VEGF for about five (5) minutes.

This "basic" program can be supplemented by supplying further signaling (i.e., in addition to the foregoing) by applying the following bioelectric signaling: (e) PDGF, HIF1a, eNOS, CXCL5 for advanced blood circulation, (f) Stem cell proliferation, (g) Stem cell differentiation control, (h) extended PRF protein release, (i) HGF for skin regeneration, and (j) EGF for skin regeneration.

A preferred treatment protocol for facial skin regeneration, rejuvenation, and/or treatment comprises: 30 minutes of bioelectric treatments (e.g., in clinic), twice a week for 16 weeks; PRF, amniotic fluid, stem cell injections (via, e.g., Dermapen™) once a week every four weeks for 16 weeks (four times total); amniotic fluid membrane application once a week every eight weeks for 16 weeks (two times total); daily bioelectric treatment (e.g., at home) for at least 15 minutes a day for 16 weeks; bioelectric micro-current conductive globe facial massage once a week every four weeks for 16 weeks (four times total); electroacupuncture once a week every eight weeks for 16 weeks (two times total); and Lumanaire hydrogel skin cream applied morning and night every day for 16 weeks.

Relationship Between the Components:

The micro voltage signal generator is attached to the pacing infusion lead with, e.g., a corkscrew tip, deep vein stimulation lead (Medtronic) (e.g., for bioelectric stimulation of the brain), or conductive polymer bandage or patch to the tissue or organ to be treated. An external signal programmer may be used to program the micro voltage signal generator with the proper signals for treatment including the COL17A1 modulating signal. The device battery may be re-chargeable with an external battery charging wand.

The essential elements are the micro voltage signal generator and the means for delivering the signal to the target tissue.

The signal generator may be external or internal. The transmission of the signal may be wireless, via liquid and/or via wires.

The tissue contact interface may be, e.g., a patch or bandage or may be via electrodes or leads. FDA cleared gel tape electrodes (Mettler) may be used for skin delivery. Electro acupuncture needles may be used to ensure the signals positively reach target tissues under the skin.

The invention is further described with the aid of the following illustrative Example.

EXAMPLES

Example I—Controlling Expression and/or Release of COL17A1

Figure 7:
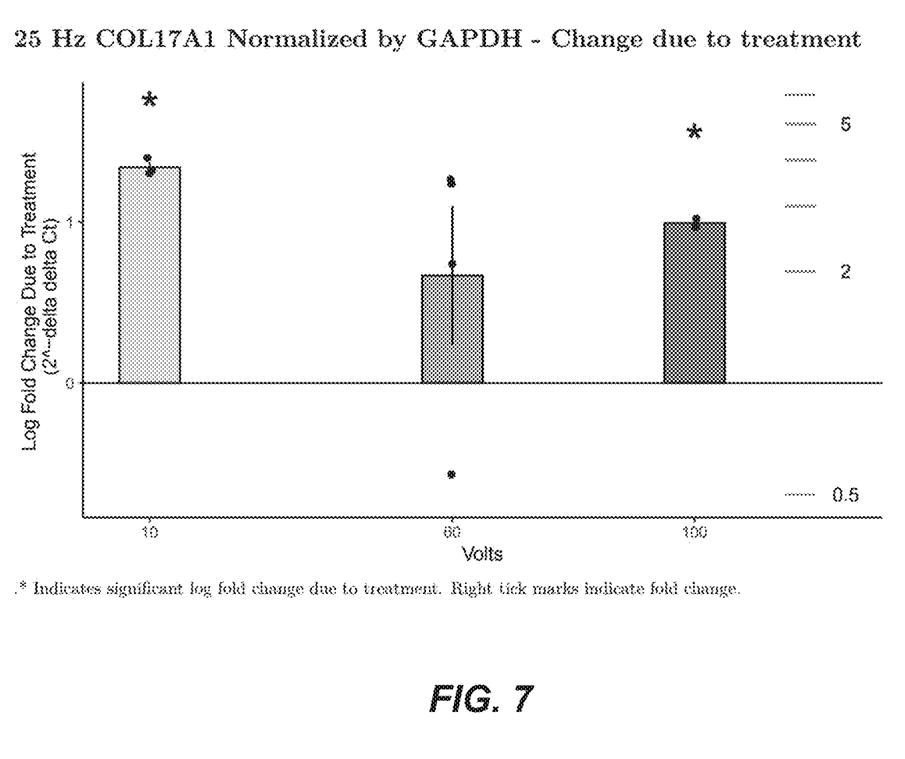
FIG. 7 is a graph from the Examples depicting the results of stimulating cellular material at 25 Hz at voltages of 10 mV, 60 mV, and 100 mV, respectively, where the horizontal lines on the right hand side of the figure reflect fold change, while the left hand side of the graph is in natural log scale.

Upregulation: It was observed that with stimulating cellular material at 25 Hz at voltages of 10 mV, 60 mV, and 100 mV, respectively, there was a considerable increase (2.4 to 3.4 fold) in COL17A1 (see, e.g., FIG. 7, 25 Hz chart—note the horizontal lines on the right hand side of the FIG. 7 reflects fold change, while the left hand side is in natural log scale).

Figure 8:
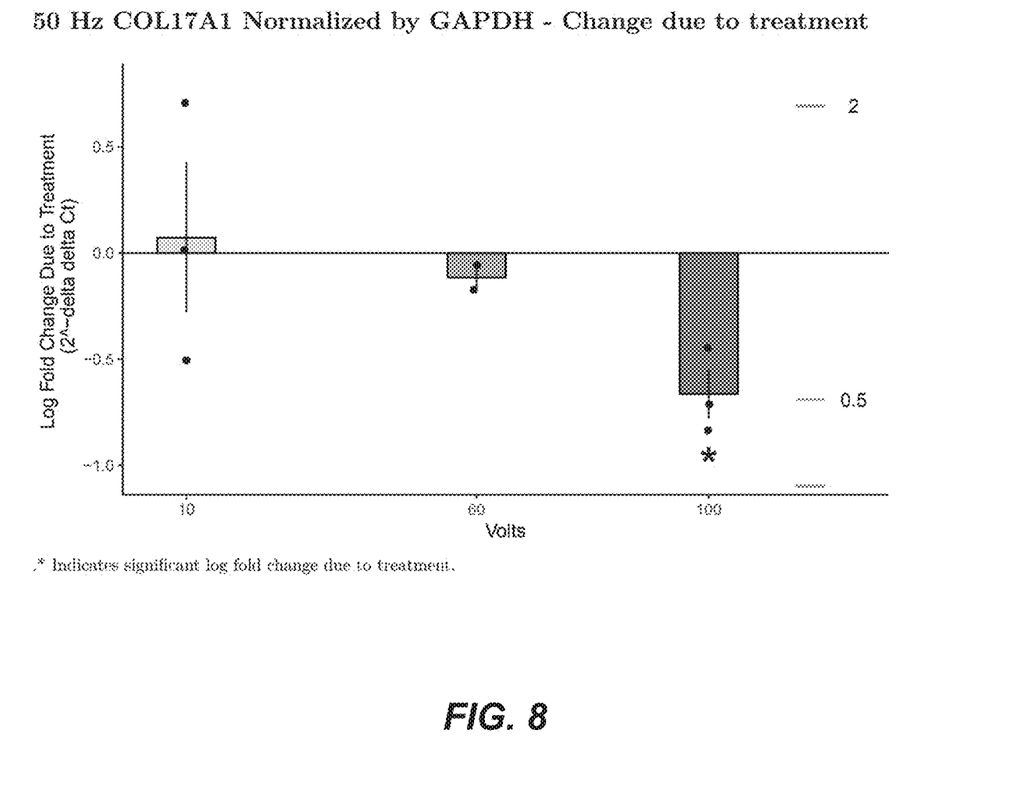
FIG. 8 is a graph from the Examples depicting the results of stimulating cellular material at 50 Hz at voltages of 10 mV, 60 mV, and 100 mV, respectively, where the horizontal lines on the right hand side of the figure reflect fold change, while the left hand side of the graph is in natural log scale.
Figure 9:
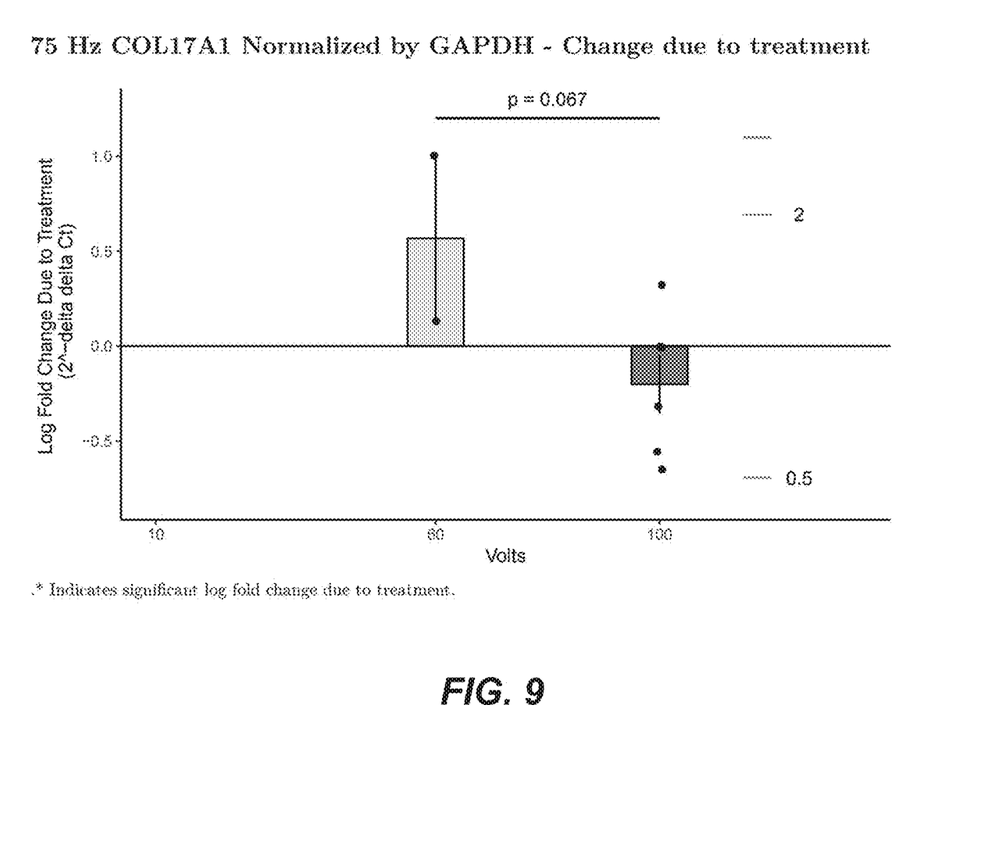
FIG. 9 is a graph from the Examples depicting the results of stimulating cellular material at 75 Hz at voltages of 60 mV and 100 mV, where the horizontal lines on the right hand side of the figure reflect fold change, while the left hand side of the graph is in natural log scale.

Narrow effective frequency margin: More importantly, stimulating at 100 mV and 25 Hz resulted in a 2.7 fold increase, while at the same voltage, but at 50 Hz, COL17A1 expression decreased by 50% (see, FIG. 8, 50 Hz chart). This is a remarkably small range in frequency where a huge difference in expression can be programmed into the cells.

The observations show that, depending on the stimulation conditions, stable and reliable gene expression changes in COL17A1 expression can be seen.

As can be seen, the best result came with a 10 mV, 25 Hz, biphasic, square-wave pulse with a 50% duty cycle. In certain embodiments, a frequency range (+/−10-20 Hz) centered about frequency signal 25 Hz may be used (e.g., 25 Hz+/−20 Hz at 10-100 mV).

Example II

Experimental Design/Methods:
Electrical Signals:
Human primary bladder fibroblast cells were plated, cultured, and stimulated (after reaching >80% confluency) for 30 minutes using a square, biphasic waveform at 50% duty using a constant voltage waveform generator RIGOL. Frequency and signal amplitudes were fixed and set from 5 Hz to 1 MHz and 1.0 V, respectively.

Target Protein: Gene expression was analyzed by extracting mRNA from osteoblasts and applying RT-qPCR assessment to quantify COL17A1 mRNA expression.

Collagen Type XVII Alpha 1 chain (COL17 A1) is a transmembrane protein that mediates the attachment of keratinocytes to the dermal-epidermal basement.

Bioelectrical stimulation had no main effect on detected COL17A1 levels in bladder fibroblast cells. Repeated one sample t-test revealed COL17A1 increased at 5,000 Hz and decreased at 250,000 Hz, but other stimulation parameters were determined to be insignificant.

According to the NCBI Gene Database, the COL 17A1 gene is not readily expressed in the urinary bladder. Based upon preliminary research, collagen type I alpha 1 chain (COL 1A1) and collagen type III alpha 1 chain (COL 3A1) have shown relevance in the urinary bladder.

REFERENCES (The contents of the entirety of each of which is incorporated herein by this reference.)

AFP=JIJI "Japanese study uncovers protein that keeps skin youthful, helping strong cells squeeze out the weak" https://www.japantimes.co.jp/news/2019/04/04/national/science-health/japanese-study-uncovers-protein-keeps-skin-youthful-helping-strong-cells-squeeze-weak/(Apr. 4, 2019).

Columbia "Implant Procedure Concepts—Pacemaker, ICD and CRT Overview," columbia.edu/itc/hs/medical/hickey/docs/Pacemaker,%20ICD%20 and %20CRT%20-Overview %20022007.pdf.

González et al. "Platelet-derived growth factor signaling modulates adult hair follicle dermal stem cell maintenance and self-renewal" *NPJ Regen Med.* 2017 Apr. 14; 2:11. doi: 10.1038/s41536-017-0013-4. PMID: 2930-2347; PMCID: PMC5665619.

Hopkins Medicine "Overview of Pacemakers and Implantable Cardioverter Defibrillators (ICDs)," hopkinsmedicine.org/healthlibrary/conditions/cardiovascular_diseases/overview_of_pacemakers_and_implantable_cardioverter_ defibrillators_icds_85,P00234/.

S. Hussein "Forever young: Study uncovers protein that keeps skin youthful" *The Jakarta Post* (Apr. 4, 2019).

Liu et al. "Stem cell competition orchestrates skin homeostasis and ageing" *Nature* 568, pp. 344-350 (April 2019).

The Mainichi "Thinning hair caused by decrease in protein: researchers" https://mainichi.jp/english/articles/20160205/p2a/00m/0na/007000c (Feb. 5, 2016).

Matsumura et al. "Hair follicle aging is driven by transepidermal elimination of stem cells via COL17A1 proteolysis" *Science*, Vol. 351, Issue 6273, aad4395 (5 Feb. 2016); DOI: aad4395.

Prochazka et al. "Cocktail of Factors from Fat-derived Stem Cells Shows Promise for Critical Limb Ischemia" http://www.sciencenewsline.com/news/2016012204520017.html (Jan. 21, 2016).

Salcedo et al. "Low current electrical stimulation upregulates cytokine expression in the anal sphincter," *Int. J. Colorectal Dis.*, 2012 February; 27(2):221-5. doi: 10.1007/s00384-011-1324-3. Epub (October 2011).

M. Schmidt "Scientists Uncover a Protein That Seems to Fight Aging in Our Skin" *Discover* (Apr. 4, 2019).

Shirai et al. "Expression of anti-aging type-XVII collagen (COL17A1/BP180) in hair follicle-associated pluripotent (HAP) stem cells during differentiation" *Tissue Cell.* 2019 August; 59:33-38. doi: 10.1016/j.tice.2019.06.001. Epub 2019 Jun. 21.

Veiga et al. "Parasacral transcutaneous electrical stimulation for overactive bladder in children: An assessment per session" *J Pediatr Urol.* 2016 October; 12(5):293.e1-293.e5. doi: 10.1016/j.jpurol.2016.03.011. Epub 2016 Apr. 16; DOI: 10.1016/j.jpurol.2016.03.011.

US Patent Publication No. US 20050113879 A1 to Schuler et al., published May 26, 2005.

US Patent Publication No. US-2019-0015661-A1 to Leonhardt et al. for "SKIN TREATMENT SYSTEM," published Jan. 17, 2019.

U.S. Pat. No. 10,646,644 to Leonhardt et al. (May 12, 2020).

What is claimed is:

1. A bioelectric stimulator programmed to produce at least one bioelectric signal that upregulates expression of COL17A1 in living target tissue, wherein the at least one bioelectric signal is a biphasic, square-wave pulse with a 50% duty cycle having a frequency of
    25 Hz (+/−20 Hz) or
    5,000 Hz
    at 10 mV to 100 mV.

2. The bioelectric stimulator of claim 1, wherein the at least one bioelectric signal has a frequency of 25 Hz (+/−10 Hz).

3. The bioelectric stimulator of claim 2, wherein the bioelectric signal is 25 Hz at 10 mV.

4. The bioelectric stimulator of claim 1, wherein the bioelectric stimulator is further programmed to produce a further bioelectric signal of 3 V/cm, 10 Hz, 2 µA (0.000002 amps), and pulse duration of 0.2 ms.

5. The bioelectric stimulator of claim 1, wherein the bioelectric stimulator is further programmed to produce a further bioelectric signal of 20 V/cm, 100 Hz, 0.25 µA (2.5e-7 amps), and pulse duration of 40 pulses/s, width of 100 µs.

6. The bioelectric stimulator of claim 1, wherein the bioelectric stimulator is further programmed to produce a further bioelectric signal of 50 Hz and 100 Hz for one (1) minute.

7. The bioelectric stimulator of claim 1, wherein the bioelectric stimulator is further programmed to produce a further bioelectric signal of 50 Hz alternating electrical field and electric current of 1 mA for 15 minutes for minutes.

8. The bioelectric stimulator of claim 1, wherein the bioelectric stimulator is further programmed to produce a further bioelectric signal applied to the target tissue of 3 mV with electric frequency of 22 Hz, and current of 1 mA for 15 minutes and 3 mA for 15 minutes.

9. A method of using the bioelectric stimulator of claim 1 to stimulate tissue of a subject to upregulate expression of COL17A1, the method comprising: connecting the bioelectric stimulator to the target tissue of the subject, and
    actuating the bioelectric stimulator to produce the programmed bioelectric signal(s) so as to stimulate the tissue and upregulate the expression of COL17A1 and thus produce collagen XVII.

10. The method according to claim 9, further comprising: delivering to the tissue a skin regeneration composition mix comprising adipose tissue-derived stem cells, exosomes, micro RNAs, hydrogel skin matrix, elastin, oxygenated nanoparticles, platelet rich fibrin ("PRF"), amniotic fluid, and growth factors.

11. The method according to claim 9, further comprising: delivering to the tissue a compound selected from the group consisting of platelet rich fibrin ("PRF"), amniotic fluid, adipose tissue-derived stem cells, a hydrogel and stem cell matrix-based skin cream, hydrogel skin matrix, oxygenated nanoparticles, and a combination of any thereof.

12. The method according to claim 9, further comprising: electrical stimulation of the tissue with conductive electro-massaging gloves,
    conducting electro acupuncture with the tissue, and/or
    delivering to the tissue LED-pulsed light therapy.

13. The method according to claim 9, further comprising: applying to the tissue amniotic fluid membrane dressings.

14. A bioelectric stimulator, wherein the bioelectric stimulator is programmed to produce at least one bioelectric signal that downregulates expression of COL17A1 in living target tissue, wherein the bioelectric signal is a biphasic, square-wave pulse with a 50% duty cycle having a frequency of:
    50 Hz at 60 mV to 100 mV,
    75 Hz (+/−10-20 Hz) at 100 mV, or
    250,000 Hz at 1 V.

15. The bioelectric stimulator of claim 14, wherein the bioelectric signal has a frequency of 50 Hz.

16. The bioelectric stimulator of claim 15, wherein the bioelectric signal is 100 mV as may be measured in the living target tissue.

17. The bioelectric stimulator of claim 14, wherein the bioelectric signal has a frequency of 75 Hz.

18. The bioelectric stimulator of claim 14, wherein the bioelectric signal has a frequency of 250,000 Hz.

19. A method of upregulating expression of COL17A1 in living target tissue to stimulate the living target tissue to produce collagen XVII, the method comprising:
    applying at least one bioelectric signal that upregulates expression of COL17A1 in the living target tissue,
    wherein the at least one bioelectric signal to upregulate expression of COL17A1 is a biphasic, square-wave pulse with a 50% duty cycle having a frequency of
    25 Hz (+/−20 Hz) or
    5,000 Hz
    at 10 mV to 100 mV as may be measured in the living target tissue, so as to stimulate the living target tissue to upregulate expression of COL17A1 and thus produce collagen XVII in the living target tissue.

20. The method according to claim 19, wherein the bioelectric signal is a 10 mV, 25 Hz, biphasic, square-wave pulse with a 50% duty cycle.

* * * * *